United States Patent [19] [11] 4,391,798
Tavss et al. [45] Jul. 5, 1983

[54] NON-IRRITATING DENTIFRICE

[75] Inventors: Edward A. Tavss, Kendall Park; Edward Eigen, East Brunswick, both of N.J.

[73] Assignee: Colgate-Palmolive Company, New York, N.Y.

[21] Appl. No.: 357,918

[22] Filed: Mar. 15, 1982

[51] Int. Cl.³ .................. A61K 9/16; A61K 9/18; A61K 7/22
[52] U.S. Cl. .................................... 424/52; 424/49; 424/54
[58] Field of Search ..................... 424/49–58, 424/359–360

[56] References Cited

U.S. PATENT DOCUMENTS

| | | | |
|---|---|---|---|
| 2,054,742 | 9/1936 | Elbel | 424/56 |
| 2,236,828 | 4/1941 | Muncie | 424/56 |
| 2,812,284 | 11/1957 | Sanders | 424/56 |
| 3,256,155 | 6/1966 | Cahn et al. | 424/56 |
| 3,548,056 | 12/1970 | Eigen et al. | 424/171 |
| 3,692,894 | 9/1972 | Amo et al. | 424/56 |
| 3,839,590 | 10/1974 | Battista | 424/49 |
| 4,058,596 | 11/1977 | Nachtigal | 424/50 |
| 4,076,800 | 2/1978 | Marsh et al. | 424/359 |
| 4,130,555 | 12/1978 | Ohtsuka et al. | 424/360 |
| 4,195,077 | 3/1980 | Marsh et al. | 424/359 |
| 4,301,141 | 11/1981 | Scheller | 424/49 |

FOREIGN PATENT DOCUMENTS 551369  2/1943 United Kingdom ............... 424/360

Primary Examiner—Shep K. Rose
Attorney, Agent, or Firm—Robert L. Stone; Murray M. Grill; Herbert S. Sylvester

[57] ABSTRACT

A dentifrice composition containing an anionic surfactant, and a minor amount of a water soluble positively charged protein hydrolysate having an isoionic point above 7, and a Bloom gel value of zero, selected from the group consisting of a protein hydrolysate fraction containing high concentrations of basic amino acids or a quaternary derivative of a protein hydrolysate, which counters the irritation to the oral tissue and reduces the bitterness caused by said anionic surfactant, without reducing its foaming and cleansing properties.

The present invention relates to novel oral compositions which are substantially non-irritating to the oral tissue, comprising an anionic surfactant and a positively charged water soluble protein hydrolysate fraction containing a high concentration of basic amino acids or a quaternary derivative of a protein hydrolysate. The protein hydrolysate fraction is obtained by extraction from a partially hydrolyzed protein mixture by means of ion exchange separation with an anion exchange resin. The quaternary derivative is obtained by quaternizing a protein hydrolysate mixture by chemically modifying the available terminal amino groups of the protein.

10 Claims, No Drawings

NON-IRRITATING DENTIFRICE

BACKGROUND AND PRIOR ART

Sodium lauryl sulfate (SLS) in dentifrices is known to cause adverse reactions to oral tissue as shown in R. C. Caldwell and R. E. Stallard, *A Textbook of Preventive Dentistry*, 196, W. B. Saunders (1977); L. J. Guarnieri, *IADR, Abstract No.* 661 (1974); and L. J. Guarnieri, *Thesis*, University of Indiana (1970). One example is gingival irritation. It is also believed that SLS is responsive for sloughing of the oral mucosa. In addition, SLS is responsible for an adverse effect on taste buds causing certain foods to have a bitter taste. Furthermore, the SLS itself, in the dentifrice tastes bitter.

U.S. Pat. No. 2,812,284 shows that the soaps and synthetic detergents in dentifrices cause a harsh and/or bitter taste, which patentee has overcome by using a mixture of two specific groups of anionic surfactants, i.e., the sulfonate salts of monoglycerides of $C_{10}$–$C_{18}$ fatty acids and the sulfate salts of $C_{10}$–$C_{18}$ fatty alcohols, in a 3:1 ratio respectively. However, the problem of oral irritation due to the presence of anionic surfactants in the dentifrice is not mentioned in aforesaid patent.

Likewise, the use of proteins in oral preparations for sundry purposes is shown in U.S. Pat. No. 1,470,794 wherein casein, gelatin and the like is present in the dentifrice as a means of retarding the rate of the production of carbonic acid. U.S. Pat. No. 2,154,168 discloses an edible dentifrice containing casein or other animal or vegetable protein adhesive carrier as a means of buffering the pH of the composition to prevent accumulations of tooth-destroying acids. U.S. Pat. No. 4,154,813 utilizes peptides as the pH adjusting means in order to combat caries which occurs at low pH. U.S. Pat. No. 4,165,368 uses galatin as a viscosity modifier to improve the flowability of the toothpaste. However, none of aforesaid patent compositions contain an anionic surfactant, nor recognize the problems of oral tissue irritation and the bitter taste associated with the presence of said anionic surfactant.

Oral compositions containing both anionic surfactants and proteins are also well known in the art as disclosed in U.S. Pat. No. 3,925,957, wherein gelatin is used as a corrosion inhibitor. In U.S. Pat. No. 3,628,974, a water insoluble partial salt of collagen is used in the formation of a stable gel for use in cosmetics containing anionic surfactants. U.S. Pat. Nos. 4,058,595 and 4,058,596 disclose stable enzymatic toothpastes containing a neutral protease and a partially hydrolyzed protein, plus anionic or nonionic surfactant.

The purposes of the proteins in the above cited patents are to impart viscosity, provide enzymatic activity, inihibit corrosion, maintain a high pH in the dentifrice, or retard the rate of development of carbonic acid. None of said proteins are reported to counter the irritation to oral mucosa caused by anionic surfactants such as sodium lauryl sulfate.

However, none of the above cited art discloses a substantially non-irritating dentifrice composition comprising an anionic surfactant and a minor amount of a water soluble hydrolyzed protein fraction rich in positively charged amino acids or a quaternized hydrolyzed protein, having an isoionic point greater than 7 and a Bloom gel value of zero.

SUMMARY OF THE INVENTION

It has been unexpectedly found that the addition of a partially hydrolyzed protein fraction rich in positively charged amino acids or a quaternized hydrolyzed protein, having an isoionic point above 7 and a Bloom gel value of zero, to an anionic surface active agent-containing dentifrice counters the adverse reactions of said anionics which include reduced gingival inflammation, reduced sloughing of the oral mucosa, reduced bitterness of foods, reduced bitterness of the dentifrice itself, but surprisingly not a concomitant loss in foaming power or detergency.

Accordingly, a primary object of present invention is to reduce the adverse effect that anionic surfactants in a dentifrice have on human oral tissue.

Another object of present invention is to provide a substantially non-irritating dentifrice of improved flavor containing an anionic surfactant and a positively charged partially hydrolyzed protein fraction rich in amino acids or a quaternized protein hydrolysate mixture.

Still another object of present invention is to provide a dentifrice wherein the foaming and detergency properties of the anionic surfactant is not decreased by the presence of the water soluble positively charged partially hydrolyzed protein fraction or the quaternized hydrolyzed protein.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel dentifrice of this invention comprises an anionic surface active agent and a water soluble positively charged partially hydrolyzed protein having an isoionic point above 7 and a Bloom gel value of zero, selected from the group consisting of a partially hydrolyzed protein fraction containing high concentrations of basis amino acids, and a qaternary derivative of a protein hydrolysate.

More specifically, present invention relates to a dentifrice composition, which may be in the form of a powder, paste or liquid, comprising an anionic surface active agent and about 0.2–5% of a positively charged partially hydrolyzed protein fraction containing high concentrations of basic amino acids obtained by extraction from a partially hydrolyzed protein mixture and isolation by ion exchange treatment with an anion exchange resin, or a positively charged quaternized hydrolyzed protein, in a dental vehicle.

The positively charged protein hydrolysate fraction utilized in present invention contains a high concentration of basic amino acids, has an isoionic point greater than 7 and a Bloom gel value of zero, and a molecular weight of about 600 to 12,000, and is a solid powdered water soluble material.

The positively charged quaternized hydrolyzed protein used in present invention is a cationic quaternary derivative of hydrolyzed collagen protein, a product of Croda Inc. of New York, known as Crotein Q, having a minimum pI of 9.5–10.5, and is an off-white free flowing powder. The free amino groups in the protein molecule react with the quaternary ammonium reactant to form the quaternized derivative.

The positively charged protein constitutes about 0.2 to 5% and preferably 0.7 to 1.3% by weight of the dentifrice containing about 0.5–5% and preferably 1–3% by weight of an anionic surfactant. Said positively charged proteins reduce the oral irritation and the bitter flavor of the anionic surfactant without decreasing the foaming and detergency properties of the composition.

The positively charged, partially hydrolyzed protein fraction having a high concentration of basic amino acids is prepared by extraction from a hydrolyzed protein mixture and isolation of the positively charged fraction by means of ion exchange treatment with an anion exchange resin. More specifically, said protein mixture is treated with an anion exchange resin, followed by dialysis. The hydrolysate fraction may be used as such or may optionally be freeze dried to remove the water therefrom. The protein mixture may be an animal collagen hydrolysate, resulting from the hydrolysis of a protein with an acid or base or enzyme. When the protein is hydrolyzed by an acid or base, it is necessary to remove the salts (NaCl) formed during said hydrolysis, prior to treatment of said protein hydrolysate mixture with the anion exchange resin. The salts can be removed by dialysis of the protein hydrolysate mixture. The source of the animal collagen hydrolysate may be leather scraps, pigs feet and hooves, bones, skin or feet of port or beef. Commercial products such as Stepan PP 37, from Stepan Chemical Co., Chicago, Illinois, an animal collagen hydrolysate hydrolyzed at high pH ($Ca[OH]_2$) from leather scraps; and Lexein 100 P from Inolex Corporation, Chicago, Illinois, an animal collagen hydrolysate from pigs feet and hooves, hydrolyzed by means of steam and/or acid followed by enzyme treatment, are typical collagen protein mixtures from which the positively charged protein hydrolysate fractions may be extracted and isolated.

More specifically, the process of preparing the positively charged protein hydrolysate fraction containing a high concentration of basic amino acids comprises the steps of treating a partically hydrolyzed protein mixture with an anion exchange resin to absorb negatively charged groups from the protein onto the resin and to substitute acetate groups or other negatively charged groups therefor on the resin and dialyzing the resultant anion-exchanged protein hydrolysate fraction to remove said resin-substituted negatively charged groups. A preferred additional first step comprises dialysis of the hydrolyzed protein mixture prior to treatment with the anion exchange resin in order to remove salts and other impurities which may be present as a result of protein hydrolysis. An optionally additional final step comprises freeze drying the positively charged protein hydrolysate fraction to remove the water therefrom and preserve it for future use. Ion exchange chromatography is a well known procedure described in the prior art. The batch phase ion exchange chromatography procedure for separation of proteins, based on charge, is described in an article by S. M. Vratsanos and I. D. Mandel entitled "Isolation of Cationic Salivary Proteins" in the Journal of Dental Research, Volume 56, B109, special issue B, 1977.

The column ion exchange chromatography method is described in a 1973 brochure by Pharmacia entitled "Sephadex ® Ion Exchangers-A Guide to Ion Exchange Chromatography". The optimal ratio of ion exchange resin to protein for fractionation of a hydrolyzed protein mixture by ion exchange chromatography is approximately 20:1. This represents the ratio of resin to protein required to just absorb the anionic proteins onto the resin, but not absorb the neutral or cationic proteins.

Any suitable anion exchange resin may be utilized in the process of producing the positively charged protein hydrolysate fractions containing a high concentration of basic amino acids. The polystyrene- and polysaccharide-based anion exchangers are most often used. The most important class of anion-exchange resins is based on the introduction of basic groups such as quaternary amino groups into a styrene-divinylbenzene copolymer after polymerization. These are strongly basic anion exchange resins. Examples of strong base anion exchangers are Dowex 1 and 2 resins by Dow Chemical Company, Amberlite IRA 401 and 410 resins of Rohm and Haas Company, De-Acidite FF and Duolites A-40 and A-42 of Diamond Shamrock Company and Bio-Rad AG 1 resin of Bio-Rad Company. Weak base anion exchangers have primary or secondary amino groups attached to the polymer lattice. Commercially available weak base anion exchangers include Dowex 3, Amberlite IR-45, De-Acidite G and Duolite A-14. Cellulose anion exchangers, such as diethylaminoethyl-(DEAE-) and epichlorhydrin-triethanolamine (ECTEOLA-) cellulose, may also be used in the fractionation process.

The positively charged, protein hydrolysate fractions of this invention are rich in positively charged amino acids as determined by their high isoionic points of about 7 to 11, whereas, proteins presently in use commercially, have isoionic points between 4 and 5. The hydrolyzed protein mixtures from which present novel positively charged protein hydrolysate fractions are extracted, such as Lexein 100 P and Stepan PP 37, have isoionic points of 4.8 and 4.3 respectively. The isoionic point (pI) is measured on a protein which has been thoroughly freed of all non-colloidal ions except hydrogen or hydroxide ions. It is the pH of the pure protein in distilled water.

Proteins generally contain a mixture of basic amine and imine groups and acidic carboxylic groups, in the form of basic and acidic amino acids. Proteins rich in basic groups are more positively charged and exhibit high pI values, whereas proteins rich in acidic groups will be less positively charged and exhibit low pI values. The positive charges are caused mainly by the arginine, lysine and histidine moieties. The negative charges are caused mainly by the aspartic and glutamic acid moieties. The overall charge is caused mainly by the ratio of the positively charged moieties to the negatively charged ones. Hence, a molecule rich is arginine, lysine and histidine, and poor in aspartic and glutamic acid would have a high positive charge. For example, glycylarginine has a positivley charged group and no negatively charged group; therefore, its positive charge is very high (pI 11). In order to obtain a protein hydrolysate fraction which contains the compound glycylarginine, the protein hydrolysate should not be dialyzed prior to being contacted with the anion exchange resin because the glycylarginine would be removed along with the inorganic salts by passing through the dialysis membrane. However, a high pI probably indicates a significant concentration of glycylarginine moieties in the positively charged ion exchange fraction.

It has unexpectedly been found that a correlation exists between the anti-irritant properties of these positively charged proteins and their pI value as evidenced by Table I, using in vitro tests. The in vitro test measures the degree of curling of epidermis strips immersed in test solutions, by measuring the width of the strip at its narrowest point where curling is most pronounced. The aqueous test solutions contain 0.15% SLS and 0.10% protein, adjusted to pH 5.3 and the strips are soaked therein at room temperature for two days prior to measuring the narrowest part of the epidermis strip.

TABLE I

| TEST MATERIAL | Isoionic POINT (pI) | Qualitative Ranking** | Curl Index*** |
|---|---|---|---|
| $H_2O$ | — | 1 | 1.01 |
| SLS + Inolex Collagen Hydrolysate Fraction $A^1$ | 8.7 | 2 | 0.78 |
| SLS + Inolex Collagen Hydrolysate Fraction $B^1$ | 7.7 | 3 | 0.64 |
| SLS + Crotein Q* | 10.0 | 4 | 0.61 |
| SLS + Whole Inolex Collagen Hydrolysate Mixture | 4.8 | 5 | 0.55 |
| SLS + Inolex Collagen Hydrolysate Fraction $C^2$ | 3.7 | 6 | 0.36 |
| SLS | — | 7 | 0.09 |
| SLS + Inolex Collagen Hydrolysate Fraction $D^2$ | 3.5 | 8 | 0.21 |

*Crotein Q is manufactured by Croda, Inc. New York,, NY; it is a cationic quaternary derivative of hydrolyzed collagen protein, more specifically described in Brochure 7778 of Croda, Inc.
**The lower the ranking number the more effective the protein in preventing skin curling by SLS.
***Ratio of half-height width of the stratum corneum to the end width; in general, the higher the number the more effective the protein in preventing skin curling by SLS.
[1] A positively charged protein hydrolysate fraction obtained by anion exchange of dialyzed Lexein 100P using BioRad AG 1 resin acetate (50–100 mesh) at a specific pH followed by neutralization to pH 7, dialysis and lyophilization. Fraction A represents the filtrate obtained at pH 12; Fraction B represents the filtrate obtained at pH 8. Neutralizations to pH 7 were made with dilute hydrochloric acid.
[2] A negatively charged protein hydrolysate fraction obtained by anion exchange of dialyzed Lexein 100P using BioRad AG 1 resin acetate (50–100 mesh) at a specific pH. Fraction C represents the material retained by the resin at pH 2; Fraction D represents the material retained by the resin at pH 4. Materials retained by the resin were removed using 2 Molar sodium chloride solution. Neutralizations to pH 7 were made with dilute sodium hydroxide.

Sodium lauryl sulfate (SLS) itself causes severe curling of the epidermis. When an anionic protein fraction is added to the SLS, the protein has no effect. However, when a cationic protein is added to SLS, the protein dramatically counters the curling effect of the SLS making this strip of epidermis similar to a strip from a water treatment. Normally one would expect that positively charged proteins would interact with negatively charged detergent molecules, thereby destroying or reducing any mildness effect caused by the protein. In fact, surprisingly it is enhanced. Although the cationic proteins neutralize the effect that SLS has on in vitro epidermis, no difference in foam height has been observed. Furthermore, the cationic proteins actually stabilize the foam height.

The dentifrice contains an anionic surface active agent to achieve increased prophylactic action and assist in achieving thorough and complete dispersion of the composition throughout the oral cavity. The anionic surface active agents contain a sulfonate, sulfate, carboxylate or phosphate as the anionic water solubilizing group. Examples of suitable anionic detergents include the soaps, such as the water soluble salts of higher fatty acids or rosin acids, such as may be derived from fats, oils and waxes of animal, vegetable or marine origin, e.g., the sodium soaps of tallow, grease, coconut oil, tall oil and mixtures thereof; and the sulfated and sulfonated synthetic detergents, particularly those having about 8 to 26, and preferably about 12 to 22, carbon atoms to the molecule. Examples of suitable synthetic anionic detergents include the higher alkyl mononuclear aromatic sulfonates such as the higher alkyl benzene sulfonates containing from 8–16 carbon atoms in the alkyl group in a straight or branched chain, e.g. the sodium salts of decyl, undecyl, dodecyl (lauryl), tridecyl, tetradecyl, pentadecyl, or hexadecyl benzene sulfonate and the $C_8$–$C_{16}$ alkyl toluene, xylene and phenol sulfonates: $C_8$–$C_{16}$ alkyl naphthalene sulfonate, ammonium diamyl naphthalene sulfonate, and sodium dinonyl naphthalene sulfonate; sulfated aliphatic alcohols such as sodium lauryl and hexadecyl sulfates, triethanolamine lauryl sulfate, and sodium oleyl sulfate; sulfated alcohol ethers, such as lauryl, tridecyl, or tetradecyl sulfates including 1–5 ethylene oxide moieties; sulfated and sulfonated fatty oils, acids or esters, such as the sodium salts of sulfonated castor oil and sulfated red oil; sulfated hydroxyamides such as sulfated hydroxyethyl lauramide; sodium salt of lauryl sulfoacetate; sodium salt of dioctyl sulfosuccinate, and the sodium salt of oleyl methyl tauride.

Also included within the ambit of the invention are the sulfuric acid esters of polyhydric alcohols incompletely esterified with higher fatty acids, e.g., coconut oil monoglyceride monosulfate, tallow diglyceride monosulfate; and the hydroxy sulfonated higher fatty acid esters such as the higher fatty acid esters of low molecular weight alkylol sulfonic acids, e.g., oleic acid ester of isethionic acid.

The anionic surfactants most often used are the ammonium, mono-, di- and triethanolamine, and alkali metal (sodium and potassium) salts of the higher alkyl benzene sulfonates, the higher alkyl sulfates, the higher fatty acid monoglyceride sulfates and the sulfated ethoxylated alcohols and mixtures thereof.

Toothpastes and toothpowders conventionally contain a substantially water insoluble polishing agent or abrasive which is compatible with the formulation. Particularly compatible materials include, for example, dicalcium phosphate dihydrate, dicalcium phosphate anhydrous, tricalcium phosphate, magnesium carbonate, calcium carbonate, calcium pyrophosphate, calcium sulfate, polymethylmethacrylate, bentonite, etc., and suitable mixtures thereof. Abrasive resinous substances such as the condensation products of melamine and urea with formaldehyde can also be used. It is preferred to use dicalcium phosphate dihydrate, dicalcium phosphate anhydrous, and calcium carbonate. The polishing agent may be the sole carrier material and is present in an amount up to about 95 percent of the carrier and generally about 20–75% of the carrier.

In toothpaste formulations the liquids and solids should necessarily be proportioned to form a creamy mass having the desired consistency which is extrudable from a pressurized container or a collapsible tube (for example, aluminum or lead). In general, the liquids in the toothpaste will comprise chiefly water, glycerine, aqueous solutions of sorbitol, propylene glycol, polyethylene glycol 400, etc., and suitable mixtures thereof. It is advantageous usually to use a mixture of both water and a humectant or binder such as glycerine or sorbitol. The total liquid content will generally be about 20–75% of the carrier. The amount of water is generally about 10–25%, preferably about 12–17% of the carrier. It is preferred to also use a gelling agent in toothpastes such as the natural and synthetic gums and gum-like materials such as Irish moss, gum tragacanth, sodium carboxymethylcelluose, polyvinylpyrrolidone, starch, and the like, usually in an amount up to about 10%, and preferably about 0.2 to 5%, of the carrier.

The carrier suitably may contain a fluorine-containing compound having a beneficial effect on the care and hygiene of the oral cavity, for example, diminution of enamel solubility in acid and protection of the teeth against decay. Examples thereof include stannous fluoride, potassium stannous fluoride ($SnF_2KP$), sodium hexafluorostannate, stannous chlorofluoride, sodium fluorozirconate, and sodium monofluorophosphate. These materials, which dissociate or release fluorine containing ions in water, suitably may be present in the carrier in an effective but nontoxic amount, usually within the range of about 0.1 to 5% by weight.

Various other materials may also be incorporated into the carrier. Examples thereof are coloring or whitening agents (for example, titanium dioxide), preservatives (for example, sodium benzoate), silicones, chlorophyll compounds, ammoniated materials such as urea, diammonium phosphate, and mixtures thereof, alcohol, menthol, and other constituents. These adjuvants are incorporated into the instant compositions in amounts which do not substantially adversely affect the properties and characteristics and are suitably selected and used in proper amount depending upon the particular type of preparations involved.

Flavoring or sweetening materials of the type commonly employed in dentifrices may be included in the carrier. Such materials, if present, aid in modifying the particular tastes of the flavor in the manner desired. Examples of such additional materials include the flavoring oils, for example, oils of spearmint, peppermint, wintergreen, sassafras, clove, sage, eucalyptus, marjoram, cinnamon, lemon, and orange, as well as methylsalicylate. Suitable sweetening agents include sucrose, lactose, maltose, sorbitol, sodium cyclamate, and saccharin. Suitably, the flavor and sweetening agent may together comprise about 0.01 to 2.0% of the carrier.

The dentifrice may be prepared by suitably mixing the ingredients. For instance in making a toothpaste, a gelling agent such as sodium carboxymethyl cellulose or Carbopol 934 and a preservative such as sodium benzoate, if employed, is dispersed in a humectant such as glycerine. Water may also be present. Additional humectant and water may then be mixed with the dispersion and a homogeneous paste, gel or cream is formed. Dental abrasive agent, surface active agent and flavor are then added. The toothpaste is then thoroughly deaerated (e.g., in vacuo) and tubed. The formulation may be deaerated during mixing or after mixing.

DETAILED DESCRIPTION OF THE INVENTION

The following examples are merely illustrative of the invention, but it is understood that the invention is not limited thereto. All amounts of various ingredients are by weight unless otherwise specified.

EXAMPLES 1-3

| Ingredient | Toothpaste % | | |
|---|---|---|---|
| | 1 | 2 | 3 |
| Dicalcium phosphate dihydrate | 50 | 50 | 50 |
| Glycerine | 20 | 20 | 20 |
| Inolex Fraction A (pI 8.7) | 1 | — | — |
| Crotein Q | — | 1 | — |
| Cellulose gum | 1.0 | 1.0 | 1.0 |
| Sodium monofluorophosphate | 0.76 | 0.76 | 0.76 |
| Flavor | 0.8 | 0.8 | 0.8 |
| Tetrasodium pyrophosphate | 0.25 | 0.25 | 0.25 |
| Sodium saccharin | 0.2 | 0.2 | 0.2 |
| Sodium lauryl sulfate | 1 | 1 | 1 |
| With water | Q.S. | Q.S. | Q.S. |

Orange juice tests on the above formulations, wherein the taste of orange juice was assessed before and after brushing with the dentifrice formulation gave the following results:

Orange juice had a pleasant taste prior to brushing with the dentifrice of Example 3, but a sour or bitter taste after brushing with Example 3 which is a flavored formulation. However, after brushing with the protein containing compositions of Example 1 and Example 2, the taste was much improved, i.e. not bitter.

Examples 1, 2 and 3 were also tasted in the absence of orange juice and compared. Example 3, with no protein, was more bitter than Examples 1 and 2.

It was additionally found that the protein containing dentifrice exhibited three times as much foaming as the non protein dentifrice.

Variations in toothpaste formulations 1 and 2 may be made by utilizing 0–5% cellulose gum, 0–5% sodium fluorophosphate, 0–5% flavor, 0–5% tetrasodium pyrophosphate and 0–5% sodium saccharin, without adversely affecting the beneficial properties as to taste, foaming and non-irritancy of the protein-containing dentifrice.

EXAMPLE 4

| Ingredient | Toothpowder % |
|---|---|
| Calcium pyrophosphate | 94.3 |
| Sodium lauryl sulfate | 3.0 |
| Stannous Fluoride | 0.5 |
| Flavor | 1.2 |
| Inolex Fraction A (pI 8.7) | 1.0 |

EXAMPLE 5

| Ingredient | Liquid Dentifrice % |
|---|---|
| Sodium lauryl sulfate | 5.0 |
| Flavor | 2.3 |
| Color | 1.5 |
| Sodium saccharin | 0.5 |
| Powered Irish moss | 1.25 |
| Inolex Fraction A (pI 8.7) | 1.0 |
| Ethyl alcohol | 10.0 |
| Water | Q.S. |

Variations in the above formulations may be made. For example, other anionic surfactants such as higher alkyl benzene sulfonates, fatty acid soaps such as tallow soap, sulfated alcohol ethers and the like may be substituted for the specific anionic surfactants in the examples.

Likewise, other positively charged protein hydrolysate fractions having a pI above 7 and obtained from other collagen hydrolysate sources may be substituted for the particular fraction used in the examples.

Other thickening or gelling agents can be substituted for the cellulose gum of the examples. Similarly, other conventional dental abrasives can replace the dicalcium phosphate abrasive such as calcium pyrophosphate, insoluble sodium metaphosphate and the like. Other fluorine-containing compounds can be substituted for the monofluorophosphate such as sodium fluoride, potassium fluoride, stannous fluoride and the like.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A substantially non-irritating dentifrice composition of improved flavor comprising an anionic surfactant, and a water soluble positively charged partially hydrolyzed protein having an isoionic point above 7, and a Bloom gel value of zero, selected from the group consisting of a protein hydrolysate fraction containing a high concentration of basic amino acids, and a quaternary derivative of the partially hydrolyzed protein, in a dental vehicle.

2. A dentifrice according to claim 1, wherein the positively charged protein hydrolysate constitutes about 0.2–5% by weight of the composition.

3. A dentifrice according to claim 2, wherein the anionic surfactant constitutes about 0.5–5% by weight of the composition.

4. A dentifrice according to claim 1, containing a positively charged partially hydrolyzed protein fraction having a high concentration of basic amino acids, prepared by extraction from a hydrolyzed protein mixture and isolation of the positively charged fraction by means of ion exchange treatment with an anionic exchange resin to absorb negatively charged groups from the protein mixture.

5. A dentifrice according to claim 1, containing a quaternary derivative of hydrolyzed collagen protein.

6. A dentifrice according to claim 1, in the form of toothpaste containing a liquid content of about 20–75% by weight of the composition.

7. A dentifrice according to claim 1, containing about 20–75% by weight of a water insoluble abrasive.

8. A dentifrice according to claim 1, containing about 0.2–5% by weight of a gelling agent.

9. A dentifrice according to claim 1, containing about 0.1–5% by weight of a fluorine-containing compound.

10. A dentifrice according to claim 1, wherein the anionic surfactant is sodium lauryl sulfate.

* * * * *